Nov. 12, 1968 D. L. ARMSTRONG Plant Pat. 2,844
ROSE PLANT
Filed June 7, 1967
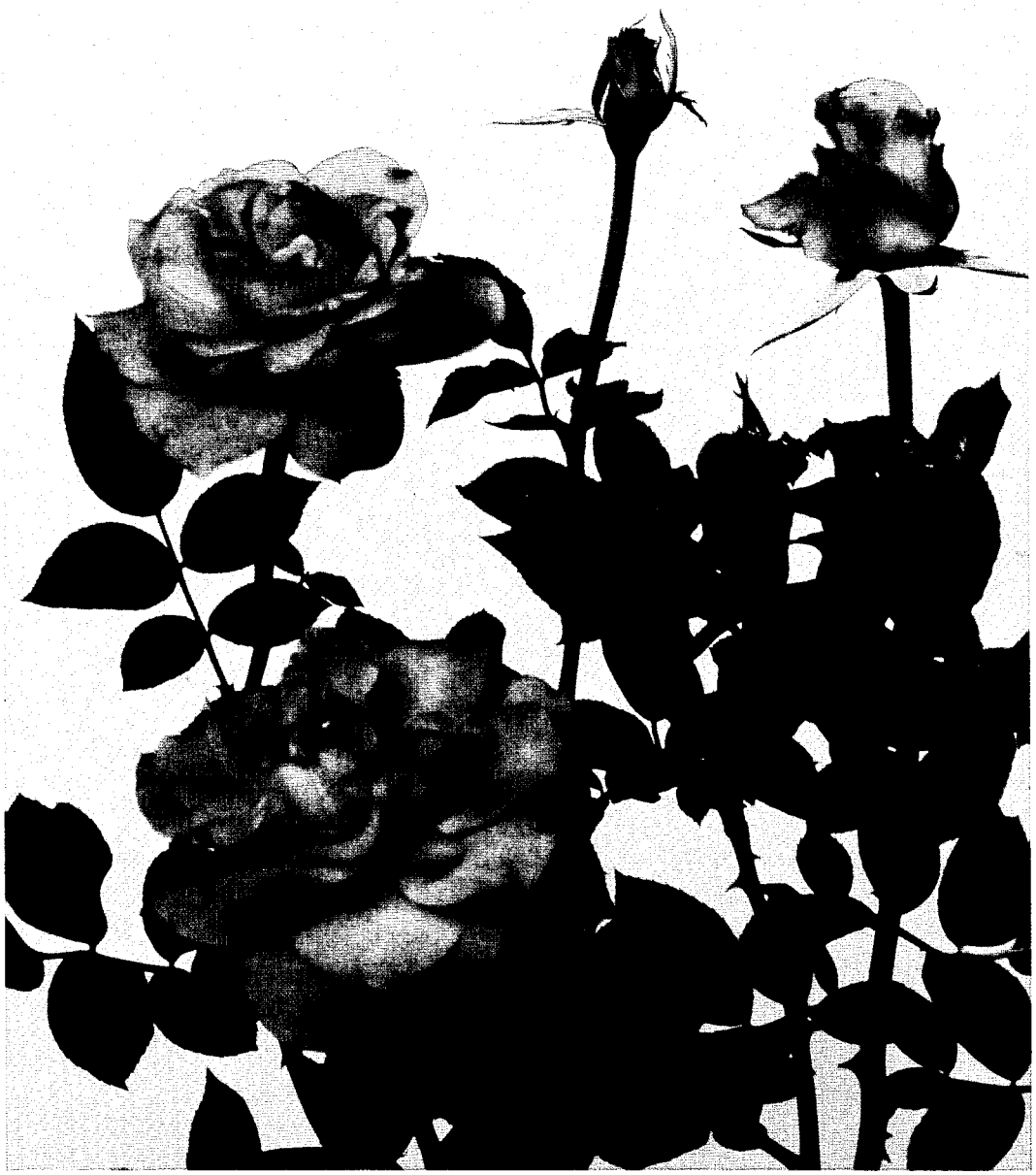
Inventor.
D. L. Armstrong
By: Robb & Robb
Attorneys.

United States Patent Office

Plant Pat. 2,844
Patented Nov. 12, 1968

2,844
ROSE PLANT

David L. Armstrong, Ontario, Calif., assignor to Armstrong Nurseries, Inc., Ontario, Calif., a corporation of California Filed June 7, 1967, Ser. No. 644,399
1 Claim. (Cl. Plt.—20)

The present invention relates to a new and distinct variety of rose plant of the grandiflora class, which was originated by me by crossing the rose variety known as "Roundelay" (Plant Patent No. 1,280) with the variety known as "El Capitan" (Plant Patent No. 1,796), the former being the seed parent and the latter being the pollen parent.

This new variety was the result of an extended breeding program having for its objective to produce improved red-flowered rose varieties in the grandiflora class. The objective was fully achieved, as evidenced by the following unique combination of characteristics which are outstanding in this new variety and which distinguish it from ts parents, as well as from all other rose vareties of which I am aware:

(1) A vigorous plant of semi-upright habit and having canes and branches heavier or of greater caliper in proportion to the plant and foliage than most garden rose varieties;

(2) Attractive, dark green, medium to large, leathery and semi-glossy foliage;

(3) A very floriferous habit, with the flowers borne on medium to long stems in small clusters, as well as singly, as exemplary of the grandiflora class;

(4) An attractive flower bud form, said buds being moderately short but quite symmetrical and high-centered and usually urn-shaped, and having excellent heavy substance, with consequent much longer lasting qualities than that of most garden roses, both on the plant and as cut flowers;

(5) Quite double flowers of medium size intermediate those of the parent varieties; and (6) A distinctive, attractive and relatively dark but bright red flower color that is resistant to fading or bluing under most weather conditions.

The new variety differs from its seed parent, "Roundelay," by having larger flowers and generally longer stems, said stems being relatively heavier or of greater caliper, and the flowers have little or no fragrance contrary to the quite definite flower fragrance of this parent.

As compared with its pollen parent, "El Capitan," the new variety bears flowers having from 10 to 15 more petals, on the average, with the petals often being smaller toward the center of the flower than in the typical flowers of this parent, and the stems of the new variety are relatively greater in caliper than the average stems of "El Capitan."

Asexual reproduction of my new variety by budding, as performed at Ontario, Calif., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated (W)) and Robert Ridgway's Color Standards and Nomenclature (hereinafter abbreviated (R)), as indicated:

Type: Tall; bush; outdoor; seedling; for cut flowers and for garden decoration.
Class: Grandiflora.
Breeding: Seedling.
*Seed parent.*—"Roundelay."
*Pollen parent.*—"El Capitan."
Propagation: Holds its distinguishing characteristics through succeeding propagations by budding.

*Flower*

Locality where grown and observed: Ontario, Calif.
Flowers borne: Sometimes singly and sometimes from two to four to stem; in irregular clusters; on strong, medium to long stems.
Quantity of bloom: Abundant, outdoors.
Continuity: Nearly continuous during growing season.
Fragrance: Slight.
Bud:
*Peduncle.*—From average length to long; heavy; erect; usually smooth; with few to several stipitate glands and none to few small prickles. Color—near Dark Olive-Buff, Plate XL (R), overlaid with near Prussian Red, Plate XXVII (R) on side exposed to sun.
*Before calyx breaks.*—Size—medium. Form—ovoid.
*As calyx breaks.*—Color—between Chrysanthemum Crimson, Plate 824, page 169 (W) and Purple Madder, Plate 1028/1, page 181 (W).
*Sepals.*—Inner surface—with fine, wooly tomentum. Outer surface—usually with few to several stipitate glands. Alternate margins—lined with fine, wooly tomentum. Other margins—with several to many stipitate glands and small, slender foliaceous parts.
*As first petal opens.*—Size—from small to average. Form—from short to medium length; from ovoid to urn-shaped. Color: outside— between Cardinal Red, Plate 822/1, page 168 (W) and Chrysanthemum Crimson, Plate 824/1, page 169 (W); Inside—between Cardinal Red, Plate 822, page 168 (W) and Chrysanthemum Crimson, Plate 824/1, page 169 (W), with small area at base of petal near Dresden Yellow, Plate 64/1, page 64 (W).
*Opening.*—Opens up well; is not retarded or prevented from opening by cold, hot, wet or dry weather.
Bloom:
*Size (when fully open).*—Average; from 3½ inches to 5 inches.
*Petalage.*—Double; from 35 to 45 petals plus 6 to 10 petaloids; arranged irregularly.
*Form.*—High-centered at first, but becoming cupped to high-centered; petals being at first tightly cupped, but later becoming more loosely flat to cupped at maturity, with tips reflexed slightly outward.
Petals:
*Texture.*—Moderately leathery.
*Appearance.*—Inside—from satiny to velvety. Outside—satiny.
*Shape.*—Outside—between round and broadly obovate, with apex flat and sometimes with 1 or 2 notches. Intermediate—broadly obovate, with apex rounded and sometimes with 1 or 2 notches. Inside—obovate, and sometimes with 1 or 2 notches.

This description of a newly opened flower was made from a rose grown outdoors during the month of October at Ontario, Calif.

*Color.*—Outer petal: outside surface—between Currant Red, Plate 821/3, page 167 (W) and Cardinal Red, Plate 822/2 (W), page 168; inside surface—between Currant Red, Plate 821/2 (W)

page 167 (W) and Cardinal Red, Plate 822/2, page 168 (W), with small area at base of petal near Dresden Yellow, Plate 64/2, page 64 (W). Intermediate petal: outside surface—near Currant Red, Plate 821/3, page 167 (W); inside surface—between Currant Red, Plate 821/1, page 167 (W) and Cardinal Red, Plate 822%1, page 168 (W), with small area at base of petal near Dresden Yellow, Plate 64%1, page 64 (W). Inner petal: outside surface—between Carmine, Plate 21, page 21 (W) and Crimson, Plate 22, page 22 (W); inside surface—between Currant Red, Plate 821/2, page 167 (W) and Cardinal Red, Plate 822/2, page 168 (W), with small area at base of petal near Dresden Yellow, Plate 64/1, page 64 (W).

This description was made from a rose that was open for three days outdoors during the month of October at Ontario, Calif.

*Color.*—Outer petal: outside surface—between Carmine, Plate 21, page 21 (W) and Cardinal Red, Plate 822/3, page 168 (W); inside surface—between Currant Red, Plate 821/2, page 167 (W) and Cardinal Red, Plate 822/3, page 168 (W), with small area at base of petal near Dresden Yellow, Plate 64/2, page 64 (W). Inner petal: outside surface—between Crimson, Plate 22, page 22 (W) and Rose Madder, Plate 23, page 23 (W); inside surface—between Carmine, Plate 21, page 21 (W) and Cardinal Red, Plate 822/3, page 168 (W).

*General color effect.*—Newly opened flower—between Currant Red, Plate 821/2, page 167 (W) and Cardinal Red, Plate 822/3, page 168 (W). Three days open—between Crimson, Plate 22, page 22 (W) and Cardinal Red, Plate 822/3, page 168 (W).

*Behavior.*—Drop off cleanly; not particularly affected by cold, hot, wet or dry weather.

*Flower longevity.*—On bush in garden—four or five days in November. Cut roses grown outdoors and kept at living-room temperatures—three or four days in November.

*Reproductive organs*

Stamens: Average number; arranged regularly about pistils; a few mixed with petaloids.

Filaments: From short to medium length (from 4 mm. to 10 mm. long); most with anthers. Color—upper ½ near Rose Bengal, Plate 25/2, page 25 (W), with remainder near Lemon Yellow, Plate 4/3, page 4 (W).

Anthers: From small to medium size; all open approximately at once. Color: upper side—margins near Saffron Yellow, Plate 7/2, page 7 (W), with remainder near Empire Yellow, Plate 603/2, page 66 (W); under side—margins near Saffron Yellow, Plate 7/2, page 7 (W), with remainder near Empire Yellow, Plate 603/2, page 66 (W).

Pollen: Moderately abundant. Color—near Tangerine Orange, Plate 9/1, page 9 (W).

Pistils: Many (approximately 90).

Styles: Uneven; from short to average length; thin; bunched. Color—upper ½ of style near Carmine Rose, Plate 621/2, page 75 (W), with remainder near Primrose Yellow, Plate 601/2, page 65 (W).

Stigma: Color—near Chinese Yellow, Plate 606/2, page 68 (W).

Ovaries: Usually all enclosed in calyx.

Hips: Average length; globular; rough; walls thick and fleshy. Color (mature)—from Apricot Orange, Plate XIV (R) to Hazel, Plate XIV (R).

Sepals: Falling soon; from medium length to long. Color: inside—near Wood Brown, Plate XL (R); outside—near Sayal Brown, Plate XXIX (R).

Seeds: From few to average number (from 12 to 20); small.

*Plant*

Foliage:

*Leaves.*—Compound of usually three to seven leaflets; abundant; from medium size to large; leathery; semi-glossy.

*Leaflets.*—Shape—broadly oval. Apex—acute. Base—round. Margin—simply serrate.

*Color.*—Mature: upper surface—near Cress Green, Plate XXXI (R); under surface—near Asphodel Green, Plate XLI (R). Young: upper surface—near Light Cress Green, Plate XXXI (R); under surface—between Grape Green, Plate XLI (R) and Asphodel Green, Plate XLI (R).

*Rachis (the supporting stem of the compound leaf).*—From average size to heavy. Upper side—grooved; with few to several stipitate glands on edges. Under side—smooth; with none to few stipitate glands and none to few small prickles.

*Stipules.*—From short to medium length; medium width; with short points turning out at an angle of usually less than 45°.

*Disease resistance.*—Better than average resistance to mildew, as determined from comparison with other rose varieties grown under comparable cultural conditions at Ontario, Calif.

Growth:

*Habit.*—Upright; spreading; much-branched.

*Growth.*—Vigorous.

*Canes.*—Heavy.

*Main stems.*—Color—near Cress Green, Plate XXXI (R). Large prickles—several; medium length; almost straight; with short to medium length, narrow base; color—near Light Drab, Plate XLVI (R). Small prickles—none. Hairs—none.

*Branches.*—Color—near Biscay Green, Plate XVII (R). Large prickles—several; short; almost straight; with short, narrow base; color—near Mikado Brown, Plate XXIX (R). Small prickles—from none to few; color—near Mikado Brown, Plate XXIX (R). Hairs—none.

*New shoots.*—Color—near Absinthe Green, Plate XXXI (R), overlaid with near Walnut Brown, Plate XXVIII (R) on side exposed to sun. Large prickles—few; short; almost straight; with short, narrow base; color—near Mineral Red, Plate XXVII (R). Small prickles—from none to few; color—near Mineral Red, Plate XXVII (R). Hairs—none.

I claim:

1. A new and distinct variety of rose plant of the grandiflora class, substantially as herein shown and described, characterized particularly as to novelty by the unique combination of a vigorous plant of semi-upright habit and having canes and branches heavier or of greater caliper in proportion to the plant and foliage than most garden rose varieties, attractive, dark green, medium to large, leathery and semi-glossy foliage, a very floriferous habit, with the flowers borne on medium to long stems in small clusters, as well as singly, as exemplary of the grandiflora class, an attractive flower bud form, said buds being moderately short but quite symmetrical and high-centered and usually urn-shaped, and having excellent heavy substance, with consequent much longer lasting qualities than that of most garden roses, both on the plant and as cut flowers, quite double flowers of medium size intermediate those of the parent varieties, and a distinctive, attractive and relatively dark but bright red flower color that is resistant to fading or bluing under most weather conditions.

No references cited.

ROBERT E. BAGWILL, *Primary Examiner.*